United States Patent
Ho et al.

(10) Patent No.: US 7,695,600 B2
(45) Date of Patent: Apr. 13, 2010

(54) TEST SYSTEM

(75) Inventors: Wah On Ho, Colchester (GB); John J. Rippeth, Ipswich (GB); Paul Chambers, Ipswich (GB)

(73) Assignee: Hypoguard Limited, Woodbridge (GB)

( * ) Notice: Subject to any disclaimer, the term of this patent is extended or adjusted under 35 U.S.C. 154(b) by 986 days.

(21) Appl. No.: 11/445,486

(22) Filed: Jun. 1, 2006

(65) Prior Publication Data
US 2007/0000777 A1 Jan. 4, 2007

Related U.S. Application Data

(60) Provisional application No. 60/687,712, filed on Jun. 6, 2005.

(30) Foreign Application Priority Data
Jun. 3, 2005 (GB) ................. 0511270.1

(51) Int. Cl.
*G01N 27/327* (2006.01)
(52) U.S. Cl. ............... 204/403.02; 204/403.04; 204/400; 204/406
(58) Field of Classification Search ................ 204/403.01–403.15, 400, 406; 205/777.5, 205/778, 792
See application file for complete search history.

(56) References Cited

U.S. PATENT DOCUMENTS

| | | | |
|---|---|---|---|
| 5,352,351 A | 10/1994 | White et al. | 204/403.14 |
| 5,582,697 A * | 12/1996 | Ikeda et al. | 205/777.5 |
| 5,708,247 A | 1/1998 | McAleer et al. | |
| 6,241,862 B1 | 6/2001 | McAleer et al. | |
| 6,436,256 B1 | 8/2002 | Williams et al. | |

(Continued)

FOREIGN PATENT DOCUMENTS

EP 1067384 A2 1/2001

(Continued)

OTHER PUBLICATIONS

Search Report, 06252538.1-1223, Sep. 20, 2006, 4 pgs.

*Primary Examiner*—Alex Noguerola
(74) *Attorney, Agent, or Firm*—O'Keefe, Egan, Peterman & Enders LLP (57) ABSTRACT

A test system for measuring analyte concentration in a fluid sample includes:

(i) a capillary-fill biosensor (20) having a working electrode (24), a reference electrode (22) and a separate counter electrode (23), arranged such that a fluid sample which flows evenly along the capillary flow path will substantially completely cover the reference electrode (22) before the fluid sample makes contact with any part of the counter electrode (23); and (ii) a test meter (42) for receiving the biosensor (20), the meter (42) including:

first signal circuitry (31) for producing a first signal when an electrical circuit is detected between the reference electrode (22) and the working electrode (24);

second signal circuitry (33) for producing a second signal when an electrical circuit is detected between the counter electrode (23) and at least one of the reference electrode (22) and the working electrode (24);

a timer (35) for determining the time interval between production of said first signal and said second signal; and a processor (32) for triggering an error condition if said time interval exceeds a preset value or if said second signal is not produced within a preset time after said first signal is produced.

16 Claims, 5 Drawing Sheets

U.S. PATENT DOCUMENTS 6,743,635 B2 * 6/2004 Neel et al. .................... 436/95
6,841,052 B2 1/2005 Musho et al.
2004/0061841 A1 4/2004 Black et al.

FOREIGN PATENT DOCUMENTS

| EP | 1281955 A1 | 2/2003 |
| EP | 1582864 A1 | 10/2005 |
| WO | WO98/55856 | 12/1998 |
| WO | WO99/13100 | 3/1999 |
| WO | WO01/73124 A2 | 10/2001 |
| WO | WO2004/008130 A1 | 1/2004 |

* cited by examiner

TEST SYSTEM

This application claims priority to U.S. provisional application Ser. No. 60/687,712 filed on Jun. 6, 2005, which is entitled "Test System" the disclosure of which is incorporated herein by reference. This application claims priority to co-pending United Kingdom patent application serial number 0511270.1 filed on Jun. 3, 2005, which is entitled "Test System" the disclosure of which is incorporated herein by reference.

BACKGROUND OF THE INVENTION

1. Field of the Invention

The present invention relates to a test system for measuring analyte concentration in a fluid sample. The invention also provides a biosensor for use in the system, notably a biosensor for measuring analyte concentration in biological fluids, for example glucose in whole blood.

2. Description of the Prior Art

Biosensors typically include an enzyme electrode comprising an enzyme layered on or mixed with an electrically conductive substrate, for example a non-mediated enzyme electrode such as described in US 2004/0061841. The electrodes respond electrochemically to the catalytic activity of the enzyme in the presence of a suitable analyte.

Electrochemical biosensors are well known in the art. They are used in measurement techniques including amperometry, coulometry and potentiometry. The biosensor comprises a working electrode and a counter electrode to complete an electric circuit. A reference electrode may also be used, to help maintain a constant potential between the working and counter electrodes. The reference and counter electrodes may be combined as a reference/counter electrode.

Typically the enzyme is an oxidoreductase, for example glucose oxidase, cholesterol oxidase, or lactate oxidase, which produces hydrogen peroxide according to the reaction:

analyte+$O_2$-[oxidase]→oxidised product+$H_2O_2$.

In an amperometric measurement, the peroxide is oxidised at a fixed-potential working electrode as follows:

$H_2O_2 \rightarrow O_2 + 2H^+ + 2e^-$.

Electrochemical oxidation of hydrogen peroxide at platinum centres on the working electrode results in transfer of electrons from the peroxide to the electrode producing a current which is proportional to the analyte concentration. Where glucose is the analyte, the oxidised product is gluconolactone.

In coulometric measurement, the current passed during completion or near completion of electrolysis of the analyte is measured and integrated to give a value of charge passed. The charge passed is related to the quantity of analyte present in a sample so that if the sample volume is known the analyte concentration can be determined. In potentiometric measurement, a potential generated by the reaction is measured at one or more points in time and related to the initial analyte concentration. The various electrochemical measurement techniques are well known to those skilled in the art.

Typically, electrochemical measurement begins automatically when the fluid sample completes an electrical circuit between the working and counter electrodes. Getting an accurate reading can be a problem when a blood sample incompletely covers the working electrode because the amount of current or measured charge is less than when the working electrode is fully covered. If a user attempts to top-up the sample by applying a second drop of blood ('double-dosing') this has the effect of reducing the precision of the measurement and increasing the response as the addition of extra blood causes a non-faradaic charging peak to occur when more of the electrode area is covered by the second sample.

It has been proposed to reduce the problem of incomplete fill by employing a pair of fill-detection electrodes in the fluid path, with the working and counter electrodes inbetween. A measurement is only taken when a circuit has been completed between the fill electrodes. However, this arrangement adds complexity to the system and does not address the problems of double-dosing by the user.

SUMMARY OF THE INVENTION

According to an aspect of the present invention there is provided a test system comprising:

(i) a capillary-fill biosensor having a working electrode, a reference electrode and a counter electrode located within a capillary flow path between a fluid inlet and a fluid outlet;

wherein the reference electrode is separate from the counter electrode, and the reference and counter electrodes are arranged such that a fluid sample which flows evenly along the capillary flow path from said fluid inlet will substantially completely cover the reference electrode before the fluid sample makes contact with any part of the counter electrode; and (ii) a test meter including:

circuitry for producing a first signal when an electrical circuit is detected between the reference electrode and the working electrode;

circuitry for producing a second signal when an electrical circuit is detected between the counter electrode and at least one of the reference electrode and the working electrode;

a timer for determining the time interval between production of said first signal and said second signal; and a processor for triggering an error condition if said time interval exceeds a preset value or if said second signal is not produced within a preset time after said first signal is produced.

The reference electrode provides a stable reference point against which the voltage of the working electrode may be measured, and enables a desired potential to be maintained between the working and counter electrodes. The system is more stable than two electrode systems with a combined counter and reference electrode. In a preferred embodiment, all three electrodes are formed from the same materials, and are preferably non-mediated electrodes. In a particularly preferred embodiment, each electrode comprises an electrically-conductive base layer comprising particles of a platinum-group metal or platinum-group metal oxide bonded together by a resin, a top layer comprising a buffer on the base layer, and a catalytically-active quantity of an oxidoreductase enzyme in at least one of the top layer and the base layer. The electrodes may be manufactured as described for the working electrode in US 2004/0061841, the contents of which are incorporated herein by reference. Manufacturing all three electrodes from the same materials and arrangement of layers simplifies the manufacturing process. We have found that the preferred system is also more sensitive and gives a more linear response than one employing electrodes which are a combination of platinised carbon and silver/silver chloride.

In a preferred embodiment, the working electrode is positioned such that a fluid sample which flows evenly along the capillary flow path from the edge will make contact with the reference electrode no later than it will make contact with the working electrode. Completion of a circuit by the fluid sample between the reference and working electrodes will signal that the fluid sample has made contact with the working electrode. Moreover, the absence of this signal will indicate that the fluid sample has not made contact with the working electrode. Under this circumstance, double dosing may be carried out without a circuit having been established between the working and reference electrodes.

The counter electrode may be located sufficiently downstream of the reference electrode to ensure that, when the counter electrode completes a circuit with the working electrode, at least a substantial portion of the working electrode will be in contact with the fluid sample. In a preferred embodiment, the counter electrode is located such that a fluid sample which flows evenly along the capillary path from the edge will substantially completely cover the working electrode before the fluid sample makes contact with any part of the counter electrode. A timer may be initiated when a first electrical circuit is completed between the reference electrode and the working electrode. If electrical contact is not made between the working electrode and the counter electrode within a specified period of time from completion of the first circuit, the meter may signal that the biosensor has received insufficient sample. Thus, the system may provide both short-fill and insufficient-fill detection.

Each electrode may be provided on either substrate, although it is preferred that all electrodes are provided on a single substrate for ease of manufacture.

The error condition may comprise a visible and/or audible warning, for example a display message warning that insufficient blood has been applied to a biosensor, optionally with an instruction to remove the biosensor from the meter and start again with a fresh biosensor. The error condition may also prevent the output of an analyte concentration value, thus preventing a reading being taken by double dosing.

It will be understood that the processor, the storage means, the signal means, the timing means, and the means for measuring the electrical property may each be provided as separate components or that any or all of them may provided in combination, for example in a single processing unit.

In a preferred embodiment, the meter has circuitry for releasably establishing an electrical connection between the reference electrode and the counter electrode. The reference electrode may therefore initially function as a combined reference/counter electrode. When a current is detected between the reference electrode and the working electrode, indicating entry of a fluid sample, the first signal causes the processor to break the electrical connection. The reference electrode then goes open circuit and no current flows. When the fluid sample reaches the working electrode, a circuit is created and the second signal is triggered.

Other aspects and benefits of the invention will appear in the following specification, drawings and claims.

BRIEF DESCRIPTION OF THE DRAWINGS

The invention will now be further described, by way of example, with reference to the following drawings in which.

DETAILED DESCRIPTION

When used herein, the following definitions define the stated term:

"Amperometry" includes steady-state amperometry, chronoamperometry, and Cottrell-type measurements.

A "biological fluid" is any body fluid in which the analyte can be measured. Examples include blood, sweat, urine, interstitial fluid, dermal fluid, and tears.

A "biosensor" is a device for detecting the presence or concentration of an analyte in a biological fluid by means of electrochemical oxidation and reduction reactions transduced to an electrical signal that can be correlated to the presence or concentration of analyte.

"Blood" includes whole blood and fluid components of whole blood, for example plasma and serum.

"Coulometry" is the determination of charge passed or projected to pass during complete or near-complete electrolysis of the analyte. The determination may be made using a single measurement or multiple measurements of a decaying current and elapsed time during electrolysis of a sample.

A "counter electrode" is one or more electrodes paired with the working electrode, through which passes a current equal in magnitude and opposite in sign to the current passed through the working electrode.

"Electrolysis" is the electrooxidation or electroreduction of a compound either directly at an electrode or via one or more mediators.

A "faradaic current" is a current corresponding to the reduction or oxidation of a chemical substance. The net faradaic current is the algebraic sum of all the faradaic currents flowing through a working electrode.

A "mediated biosensor" is a biosensor which includes a significant quantity of a mediator.

A "mediator" is an electron carrier which, in an oxidised form, accepts electrons from an enzyme and then, in a reduced state, transports the electrons to an electrode where it becomes re-oxidised. Examples of mediators include ferrocene, ferrocene derivatives, ferricyanide, osmium complexes, 2,6-dichlorophenolindophenol, Nile Blue, and Medola Blue; see, for example: U.S. Pat. Nos. 5,708,247, 6,241,862, 6,436,256, WO 98/55856, and WO 99/13100.

A "non-mediated biosensor" is a biosensor which does not include a significant quantity of a mediator.

"Potentiometry" is the measurement of electrical potential under conditions of low or no current flow, which may be used to determine the presence or quantity of analyte in a fluid.

A "reference electrode" is an electrode that has a substantially stable equilibrium electrode potential. It can be used as a reference point against which the potential of other electrodes, notably the working electrode, can be measured.

A "working electrode" is an electrode at which analyte undergoes electrolysis.

Preparation of BSA-Pt/Carbon

In a 250 ml glass bottle, 6.4 g of BSA, Miles Inc. was dissolved in 80 ml of phosphate buffered saline (PBS) and 20 g of 10% Pt/XC72R carbon, MCA Ltd, was gradually added with constant stirring. The bottle was then placed on a roller mixer and allowed to incubate for two hours at room temperature.

A Buchner funnel was prepared with two pieces of filter paper, Whatman™ No 1. The mixture was poured into the funnel and the carbon washed three times with approximately 100 ml of PBS. The vacuum was allowed to pull through the cake of carbon for about 5 minutes to extract as much liquid as possible. The cake of carbon was carefully scraped out into a plastic container and broken up with a spatula. The carbon was then placed in an oven at 30° C. overnight to dry. The purpose of this procedure is to block active sites on the carbon hence to aid the shelf stability and reproducibility of the carbon's properties.

Preparation of Platinum Group Metal/Carbon Inks

BSA-Pt/Carbon was prepared in Metech 8101 polyester resin as the polymer binder and Butyl Cellosolve Acetate (BCA) as a solvent for the ink.

| Ink Formulation | |
|---|---|
| Metech 8101 resin | 44.68% |
| BSA-Pt/Carbon | 18.42% |
| graphite | 9.64% |
| BCA/cyclohexanone | 22.94% |
| Tween ® 20 | 2.94% |
| glucose oxidase | 1.38% |

Tween 20 is a surfactant supplied by Sigma-Aldrich. Tween is a registered trade mark of ICI Americas, Inc. The solvent is a 50% v/v mixture of BCA and cyclohexanone. The graphite was Timrex KS 15 (particle size <16 μm), from GS Inorganics, Evesham, Worcs. UK.

The resin, Tween 20, and about half the solvent were initially blended together prior to adding the carbon fraction and the graphite. Initially the formulation was hand-mixed followed by several passes through a triple roll mill. The remaining volume of solvent was then added to the ink and blended to bring the ink to a suitable viscosity for printing.

Preparation of Drop-Coating Solutions

The coating solution is water-based and consists of a high concentration of buffer, preferably phosphate at pH 8. It has been found that buffering capacity is more important than ionic strength. In this example the solution contains glucose oxidase and a system stabiliser, in this example trehalose.

| Drop-Coat Solution | | | |
|---|---|---|---|
| Buffer | KH$_2$PO$_4$/K$_2$HPO$_4$ | 385 mM, pH 8 | Sigma |
| Enzyme | Glucose oxidase | 4080 U/ml | Biozyme |
| Stabiliser | Trehalose | 1% | Sigma |
| Preferred Ranges | | | |
| Buffer | 300-1000 mM, pH 7-10 | | |
| Enzyme | 500-12000 U/ml (1.85-44.4 mg/ml) | | |
| Stabiliser | 0.5-30% | | |

The activity of the glucose oxidase is about 270 units per milligram of material (360 units/mg of protein because the enzyme comes in a preparation with other lyophilisation and stabilisation agents).

If the enzyme is located in the base layer the drop coating solution may contain only buffer, optionally with the stabiliser.

Methods of Manufacture

Glucose test strips (biosensors) were manufactured using a combination of screen printing and drop coating technologies. Other printing and/or coating technologies, well known per se to those skilled in the printing and coating arts may also be used. The exemplified methods are by way of illustration only. It will be understood that in each case the order of performance of various steps may be changed without affecting the end product. For each of FIGS. 1-2 the top row illustrates a process step, and the bottom row illustrates the sequential build-up of the biosensor.

Figure 1:
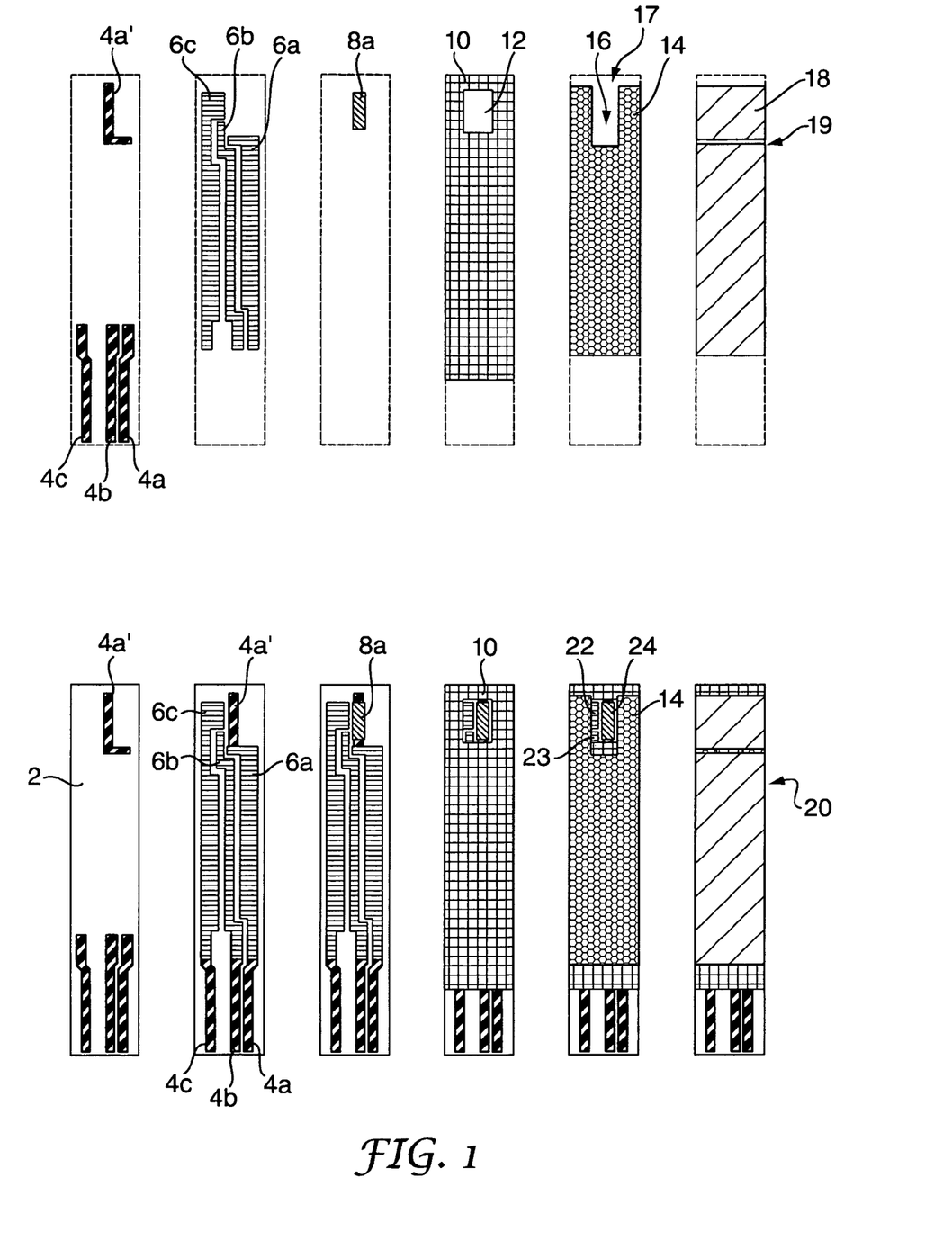
FIGS. 1 and 2 show stages in the formation of a biosensor in accordance with aspects of the present invention.

To manufacture the biosensor shown in FIG. 1, a base substrate 2 is formed from a polyester material (Valox™). Conductive tracks 4 were printed onto the substrate 2 as a Conductive Carbon Paste, product code C80130D1, Gwent Electronic Materials, UK. In this embodiment, tracks 4a, 4b and 4c provide electrical contacts for connecting, respectively, the working electrode 24, the counter electrode 23 and the reference electrode 22 to a meter (not shown). Conductive track 4a' is printed to provide a conductive surface on which the working electrode 24 will be formed. After printing, the ink of the conductive tracks 4 was dried for 1 minute in a forced air dryer at 130° C. The second ink printed on top of the conductive carbon 4 is a Silver/Silver Chloride Polymer Paste, product code C61003D7, Gwent Electronic Materials, UK. In this example, track 6a connects the conductive carbon tracks 4a and 4a'; tracks 6b and 6c are connected to the respective conductive carbon tracks 4b and 4c, and will provide, respectively, the counter electrode 23 and the reference electrode 22. The ink 6 is dried at 130° C. in a forced air dryer for 1 minute.

The next layer is the platinum group metal carbon ink which is printed onto the conductive carbon 4d where the working electrode 24 is to be formed. This ink is dried for 1 minute at 90° C. in a forced air dryer to form a conductive base layer 8a about 12 μm thick. A dielectric layer 10 is then printed, excluding a working area 12 in which the working 24 and reference 22 electrodes are to be located. The dielectric layer 10 is MV27, from Apollo, UK. The purpose of this layer is to insulate the system. It is dried at 90° C. for 1 minute in a forced air dryer. If desired, the base layer 8a can alternatively be printed after the dielectric layer 10. However, it is preferred to print the base layer 8a first, since the subsequent application of the dielectric layer 10 removes some of the tolerance requirements of the print.

A drop-coat layer is applied to the base layer 8a using BioDot drop-coating apparatus. The volume of drop-coating solution used is 125 nl, applied as a single droplet; the drop-coat layer is dried in a forced air dryer for 1 minute at 50° C. to form the working electrode 24. After drop-coating, the partially-constructed test strips were allowed to condition for four days at room temperature and low humidity. A spacer layer 14 is formed by screen-printing a UV-curable resin (Nor-Cote 02-060 Halftone Base) on the dielectric layer 10 and then curing the resin with UV light (120 W/cm medium pressure mercury vapour lamp) at up to 30 m/min. The resin comprises acrylated oligomers (29-55%) N-vinyl-2-pyrrolidone (5-27%) and acrylated monomers (6-28%). The spacer 14 has a channel 16 which will determine the capillary flow path of the biosensor. A second substrate, or lid, 18 is adhered to the spacer 14 to produce the biosensor 20. The lid 18 comprises a 50 μm PET tape (Adhesive Research 90119) coated with about 12.5 μm of a hydrophilic heat-seal adhesive 'HY9'. The lid 18 is adhered to the spacer 14 by the action of heat and pressure (100° C., 400 kPa) for 1-2 seconds. The lid 18 is provided with a narrow vent 19 to permit the exit of air from the capillary flow path. The vent 19 need not extend right across the lid 18 but could comprise a hole or short slot in fluid communication with the capillary flow path. If desired, the second substrate 18 may be laid over a number of substrates on which the above steps are carried out, followed by guillotining of the lid 18 to produce the biosensor 20. Alternatively the spacer 14 could be initially adhered to the second substrate 18 and then adhered to the first substrate. A benefit of this arrangement is that the second substrate 18 may be cut to provide the vent 19 while both parts of the second substrate 18 are held in the correct positions by the spacer 14.

The biosensor 20 has a reference electrode 22, a counter electrode 23 and a working electrode 24 which are defined by the working area 12 in the dielectric layer 10. The working electrode 24 comprises the base layer 8a on a conductive carbon layer 4a' on the first substrate 2, and a top layer including the buffer.

In large-scale manufacturing, a plurality of substrates may be provided initially connected together on a single blank or web, preferably two substrate-lengths deep, and the various processing steps carried out on the entire blank or web, followed by a final separation step to produce a plurality of biosensors 20.

The biosensor 20 has a capillary flow path defined by the channel 16 in the spacer 14, the inner surface of the lid 18, and the first substrate 2 (largely covered by the dielectric layer 10). The flow path extends from an inlet 17 at the parallel short edges of each of the substrates 2, 18 to the reference, counter and working electrodes 22, 23, 24. The inner surface of the lid 18 is treated to be hydrophilic to facilitate wetting by blood. With glucose oxidase as the enzyme, the biosensor is used to measure blood glucose. A user may take a reading by pricking an alternative site such as his or her upper arm to produce a small drop of blood on the skin, and touching the appropriate short edge of the biosensor 20 to the skin where the blood is located. The blood is drawn rapidly to the working area 12, producing a current readable by a meter connected to the conductive tracks 4a, 4b, 4c in a known manner. A sample volume of about 0.8 nl is sufficient. However, if an insufficient sample volume is applied, an inaccurate reading may result. Application of a second sample will then cause a non-faradaic charging peak, as will be discussed later.

Figure 2:
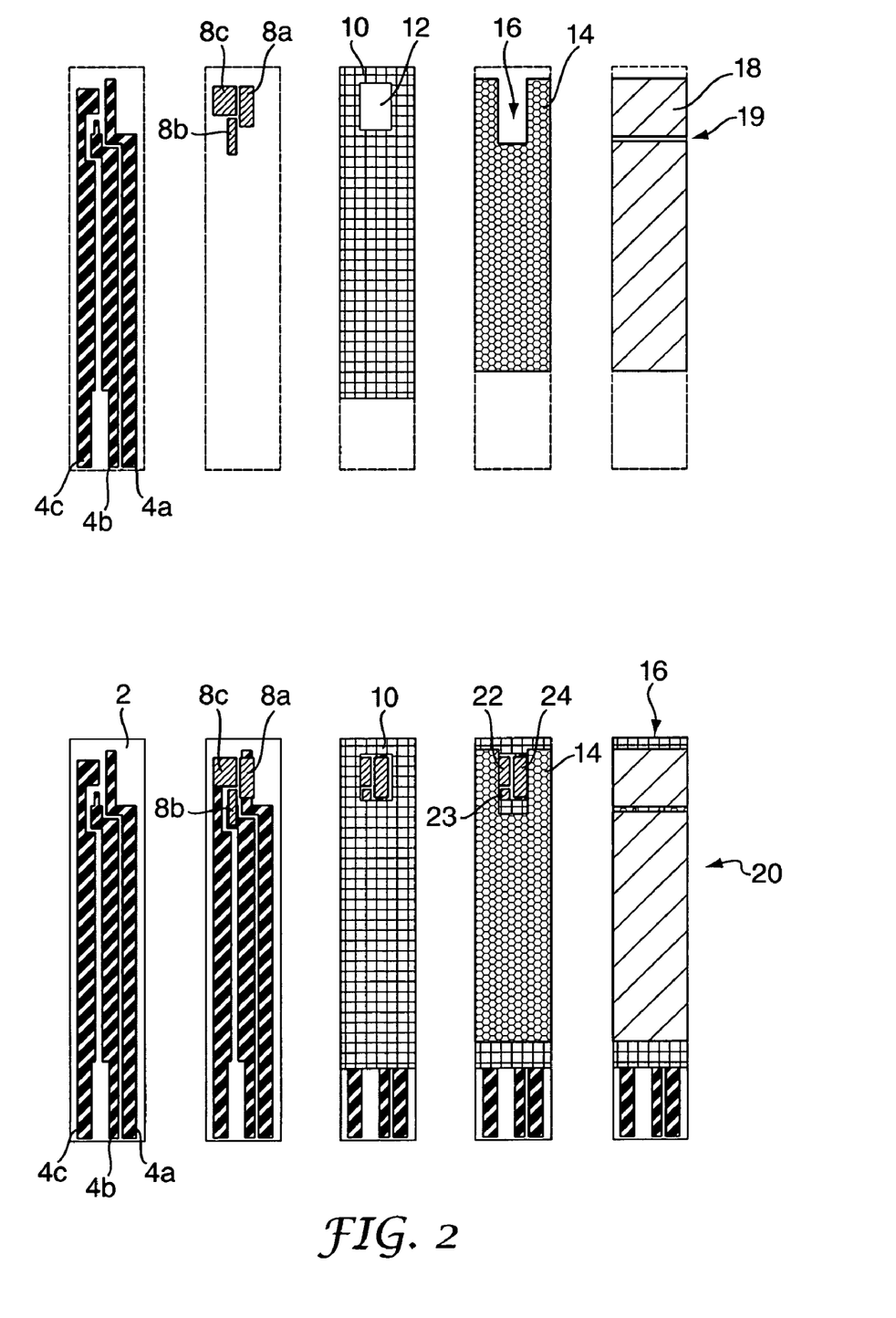

Referring now to FIG. 2, an alternative embodiment of biosensor is shown. In this embodiment, the conductive carbon tracks 4a, 4b, 4c extend to the working area 12, and Ag/AgCl tracks are not used. Each track 4a, 4b, 4c is printed with a base layer 8a, 8b, 8c respectively, using the same formulation and printing method as for the base layer 8a of FIG. 1. The further processing steps are identical to those for FIG. 1, with the drop coat being applied only to the base layer 8a which will form the working electrode 24. However, for manufacturing convenience it would also be possible to apply the top coat to all of the base layers 8a, 8b and 8c, using any convenient coating or printing technique, thereby removing the need for accurate positioning of a droplet on a precise area 8a.

Figure 5:
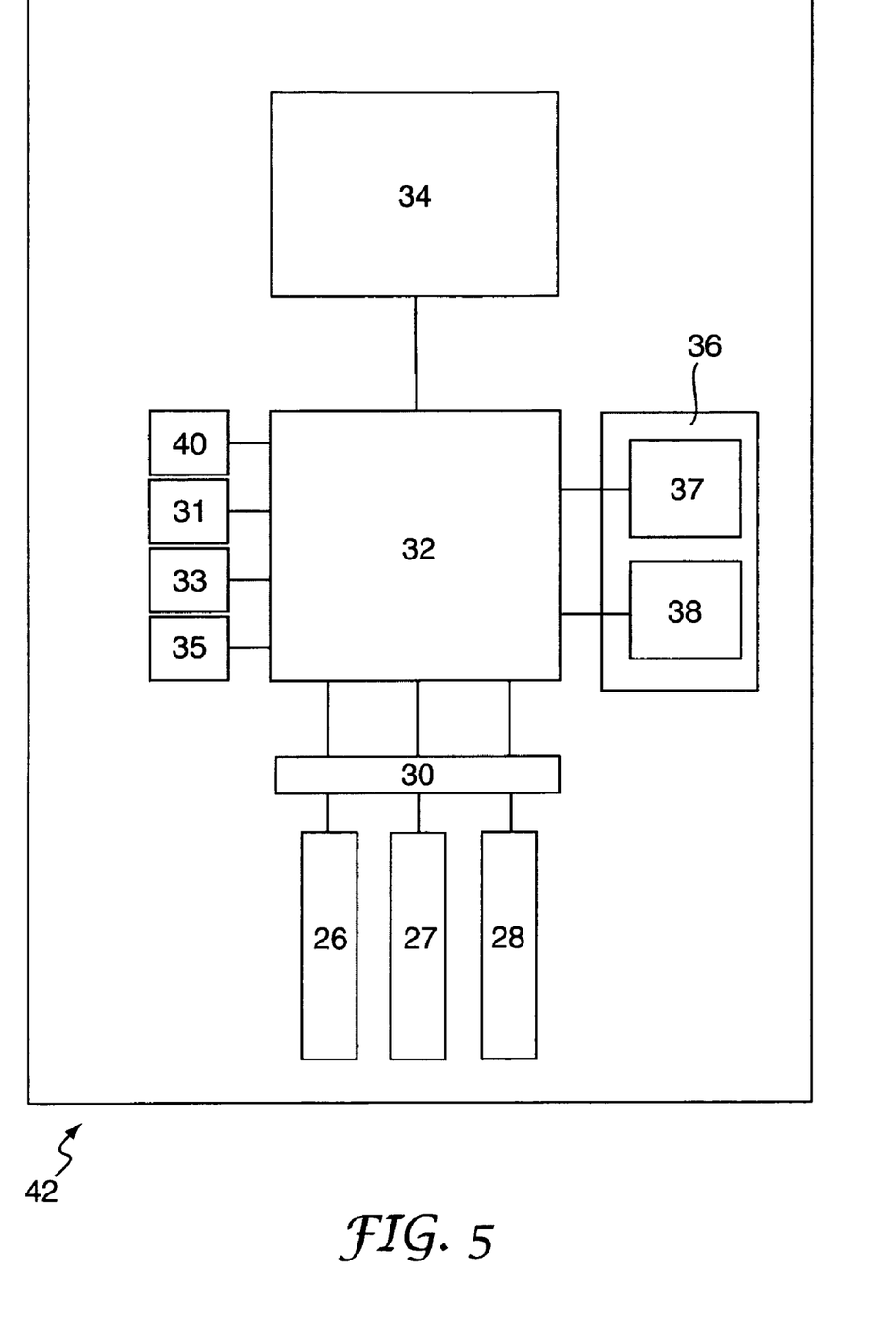
FIG. 5 is a schematic representation of a meter for use with the biosensors of FIGS. 1 and 2.

A meter 42 suitable for use with the biosensors 20 is shown schematically in FIG. 5. The meter 42 has electrode contacts 26, 27, 28 for making contact, respectively, with the electrode tracks 4a, 4b, 4c on the biosensor 20. Electrical values are communicated to a processor 32 via an A/D converter 30. The processor 32 can selectively access first storage means 37 storing calibration data relating to whole blood and, optionally, to second storage means 38 storing calibration data relating to a control solution. In this example, the calibration data 37, 38 are contained on a code chip 36 which is provided with a pot of biosensors 20. The processor 32 has a temperature sensor 40, and calibrates output analyte values using the measured temperature and calibration data 37 or 38. The calculated analyte value is displayed on an LCD 34.

When an analyte measurement is to be made, a biosensor 20 is inserted into the meter 42 so that the electrode tracks 4a, 4b, 4c make electrical contact with the respective electrode contacts 26, 27, 28. Insertion of the biosensor 20 completes a circuit and activates the meter 42 to expect a measurement within a specified time, in this example, two minutes. To take a blood glucose measurement, a user pricks a finger or alternative site such as the upper arm, to provide a drop of blood, and touches the free end of the biosensor 20 against the drop. Capillary forces draw the blood sample into the biosensor via the channel 16 of the capillary flow path. The arrangement of electrodes is such that the blood sample makes contact with the working electrode 24 no later than it makes contact with the reference electrode 22. When the sample makes contact with both the reference 22 and working 24 electrodes this completes a circuit and alerts the processor 32 that a sample has made contact with the working electrode 24. The processor 32 includes first signal means 31 for producing a first signal when this circuit is completed. The processor 32 also comprises a timer 35 which measures the time from when the first signal is produced.

Further flow of the fluid sample down the channel 16 of the capillary flow path brings the sample into contact with the separate counter electrode 23. This completes an electric circuit between the counter electrode 23 and/or the reference electrode 22 and the working electrode 24, and alerts the processor 32 that the sample has wholly or sufficiently covered the working electrode 24 for a reading to be taken. The processor 32 includes second signal means 33 for producing a second signal when this second circuit is completed. If the second signal is not produced within a pre-set time, for example five seconds, after the first signal, the processor will trigger an error condition which will be displayed on the LCD 34. The user will be prompted to remove the used biosensor 2 and begin again with a fresh biosensor. If insufficient sample is present to produce the second signal, the user may be able to augment the sample by applying a second drop of blood. This double-dosing does not generate a non-faradaic charging peak because the circuit has not yet been completed between the working and counter electrodes. When the second signal has been produced within the pre-set time, the working electrode is polarised, for example to 350 mV or 375 mV, and an electrochemical measurement, in this example an amperometric measurement, is made.

It will be understood that the first signal means 31 and the second signal means 33 may be provided by one and the same circuitry, and that the processor 32, the signal means 31, 33, timer 35, and storage means 37, 38 may each be provided as separate components or that any or all of them may be provided in combination, for example in a single processing unit.

Figure 6:
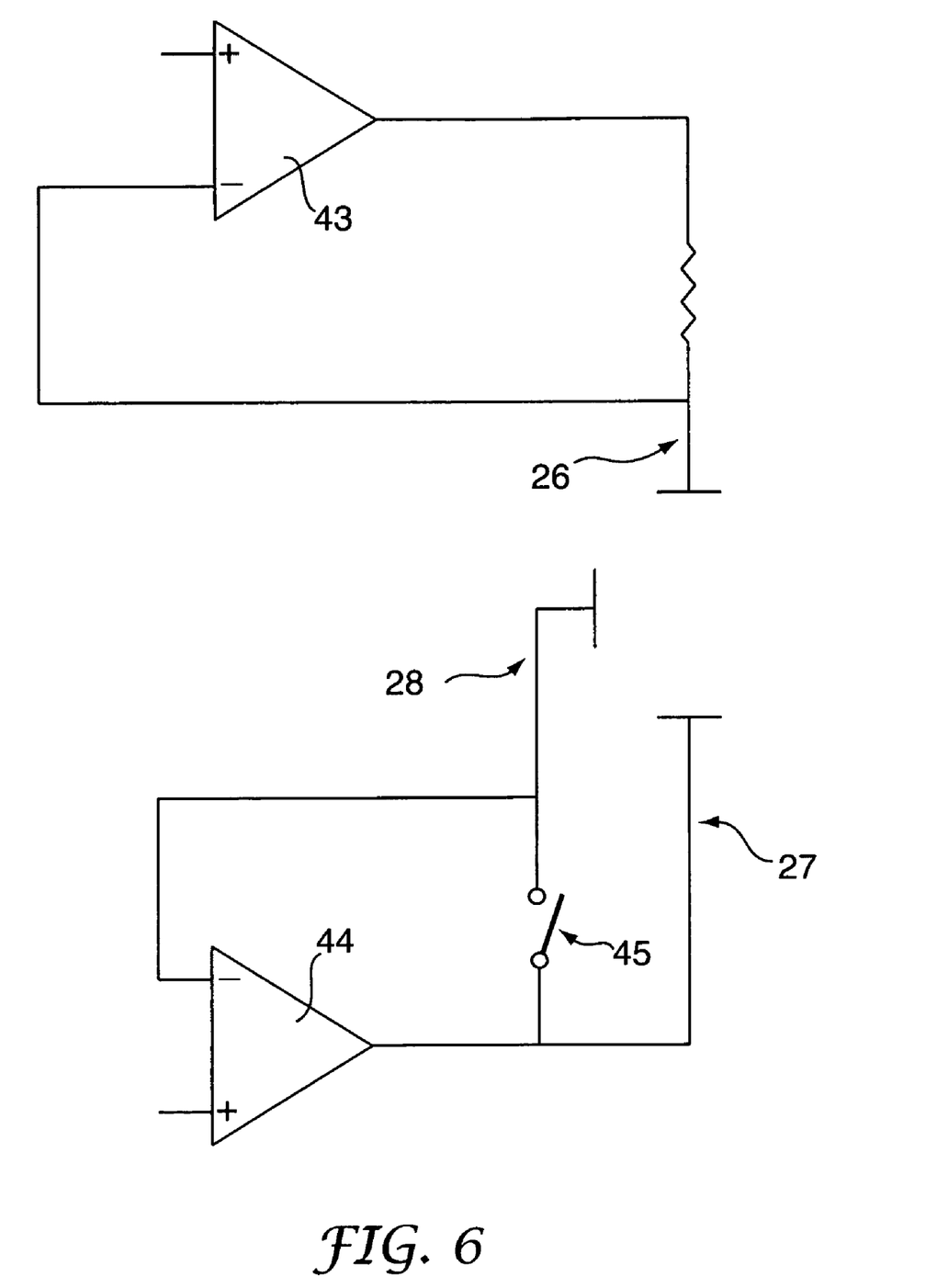
FIG. 6 is a circuit diagram of a potentiostat circuit for the meter of FIG. 5.

Referring now to FIG. 6, a potentiostat circuit for a meter in accordance with a preferred embodiment is illustrated. The circuit has a first op-amp (43) and a second op-amp (44). 43 sets the polarising potential at the working electrode (WE) relative to the reference electrode (RE). At the start of a test, a switch 45 is made between contacts 27 and 28, thereby establishing a normal combined reference/counter electrode configuration. When blood is applied and establishes an electrical connection between the reference and working electrodes, a current will flow. This current is detected and the switch 45 is released. After the switch is released no current will flow because the reference electrode will be open circuit and the output of 44 will be at the same voltage as the working electrode. When the blood sample reaches the reference electrode, a feedback loop is made and normal operation of the potentiostat circuit is resumed. When this happens the strip has been filled with enough blood.

Figure 3:
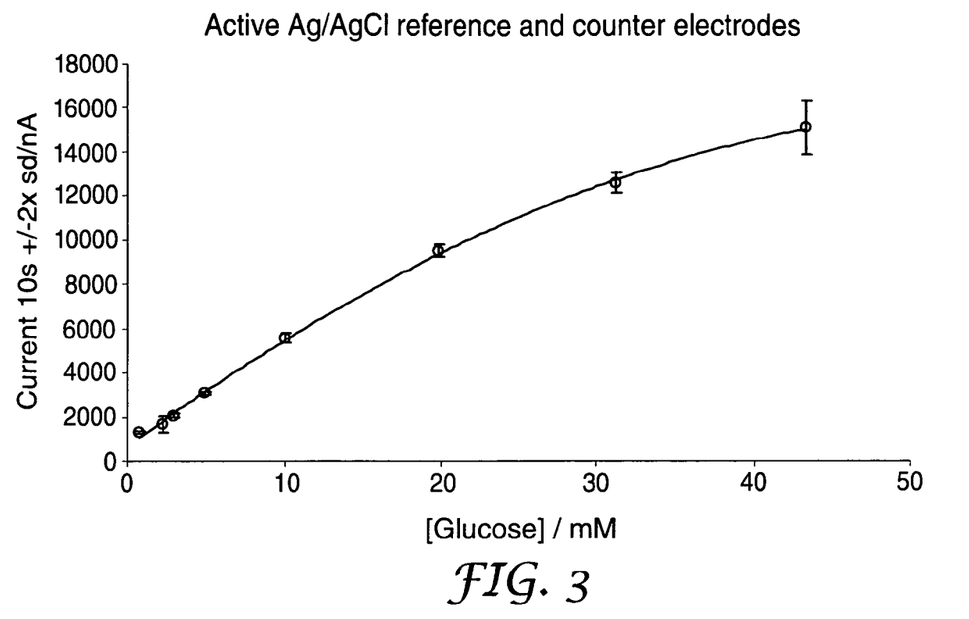
FIGS. 3 and 4 are graphs showing current responses of the biosensors of, respectively, FIGS. 1 and 2 for samples of venous blood having different glucose concentrations.
Figure 4:
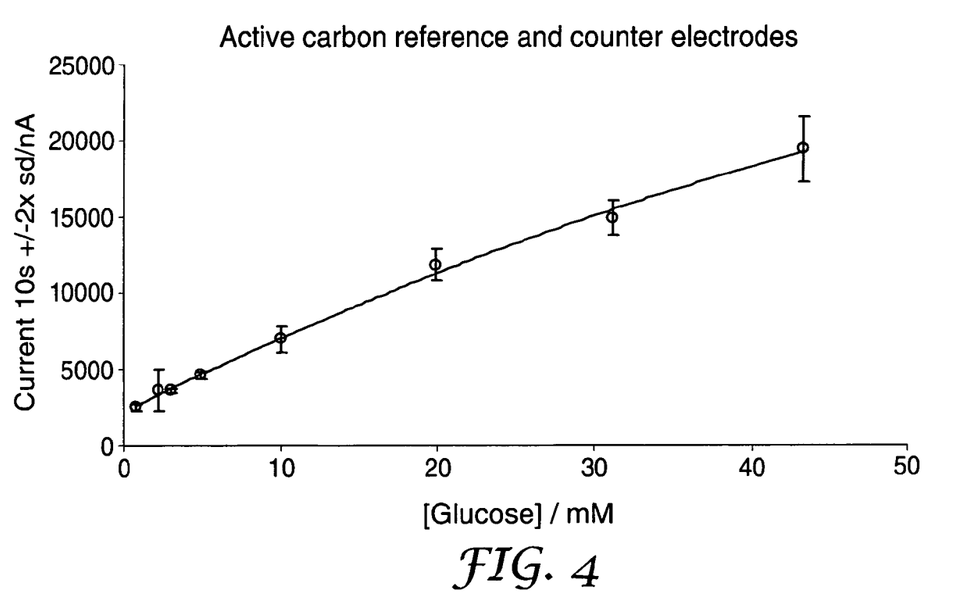

Test results for the biosensor of FIG. 1 are shown in FIG. 3, and test results for the biosensor of FIG. 2 are shown in FIG. 4. In both cases, the drop-coat solution was applied by drop-coating onto the base layer 8a to form the working electrode 24, but not onto the reference electrode 22 or counter electrode 23. However, it would be possible to apply the drop-coat solution to either or both of the other electrodes, or over the entire working area 12 if convenient to do so. Both biosensors give an acceptable response curve of current -v- glucose concentration, but the biosensor of FIG. 2, in which all three electrodes comprise the base layer 8 of platinised carbon, gives a higher background current and is more sensitive and has a more linear response.

It is appreciated that certain features of the invention, which are for clarity described in the context of separate embodiments, may also be provided in combination in a single embodiment. Conversely, various features of the invention which are, for the sake of brevity, described in the context of a single embodiment, may also be provided separately or in any suitable subcombination.

While the present invention has been described with reference to specific embodiments, it should be understood that modifications and variations of the invention may be constructed without departing from the spirit and scope of the invention defined in the following claims.

What is claimed is:

1. A test system comprising:
   (i) a capillary-fill biosensor for indicating electrochemically the catalytic activity of an enzyme in the presence of a fluid sample containing an analyte acted upon by said enzyme;
   the biosensor having a fluid inlet, a fluid outlet, and a capillary flow path connecting the fluid inlet and the fluid outlet;
   the biosensor further including a working electrode, a reference electrode and a counter electrode located within the capillary flow path;
   the working electrode including a catalytically-active quantity of said enzyme;
   wherein the reference electrode is separate from the counter electrode, and the reference and counter electrodes are arranged such that a fluid sample which flows evenly along the capillary flow path from said fluid inlet will substantially completely cover the reference electrode before the fluid sample makes contact with any part of the counter electrode; and
   (ii) a test meter for receiving said biosensor, the meter comprising:
   contacts for making electrical contact with each electrode on said biosensor;
   circuitry for performing an electrochemical measurement on said biosensor to produce a measured electrochemical value;
   circuitry for determining an analyte concentration value for a specified biological fluid from said measured electrochemical value; and
   circuitry for indicating a determined analyte concentration value;
   the meter further comprising:
   first signal circuitry for producing a first signal when an electrical circuit is detected between the reference electrode and the working electrode;
   second signal circuitry for producing a second signal when an electrical circuit is detected between the counter electrode and at least one of the reference electrode and the working electrode;
   a timer for determining the time interval between production of said first signal and said second signal; and
   a processor for triggering an error condition if said time interval exceeds a preset value or if said second signal is not produced within a preset time after said first signal is produced.

2. A system according to claim 1, further comprising:
   a switch for releasably connecting the reference electrode and the counter electrode, the switch being closed before an electrical circuit has been detected between the reference electrode and the working electrode; and
   circuitry for opening the switch when an electrical circuit has been detected between the reference electrode and the working electrode.

3. A system according to claim 2, wherein said circuitry for opening the switch is a potentiostat circuit which makes a feedback loop when an electrical circuit has been made between the working electrode and the counter electrode.

4. A system according to claim 2, wherein the reference electrode will go open circuit when the switch is opened.

5. A system according to claim 1, wherein the biosensor comprises:
   a first substrate;
   a second substrate overlying at least a part of the first substrate;
   the working electrode, the counter electrode, and the reference electrode each being provided on either one of the substrates;
   conductive tracks connected to said working, counter and reference electrodes for making electrical connections with a test meter apparatus;
   a spacer layer having a channel therein and disposed between the first substrate and the second substrate, the spacer layer channel co-operating with adjacent surfaces to define the capillary flow path which extends from an edge of at least one of said substrates to said electrodes.

6. A system according to claim 1, wherein each of said electrodes is non-mediated and includes a base layer comprising particles of a platinum-group metal or platinum-group metal oxide bonded together by a resin.

7. A system according to claim 6, wherein each of said electrodes further includes a top layer comprising a buffer on the base layer, and a catalytically-active quantity of an oxidoreductase enzyme in at least one of the top layer and the base layer.

8. A system according to claim 1, wherein the counter electrode is downstream of the working electrode in the capillary flow path.

9. A system according claim 1, wherein the working electrode is positioned such that a fluid sample which flows evenly along the capillary flow path from said edge will make contact with the reference electrode no later than it will make contact with the working electrode.

10. A test system comprising:
    (i) a capillary-fill biosensor having a working electrode, a reference electrode and a counter electrode located within a capillary flow path between a fluid inlet and a fluid outlet;
    wherein the reference electrode is separate from the counter electrode, and the reference and counter electrodes are arranged such that a fluid sample which flows evenly along the capillary flow path from said fluid inlet will substantially completely cover the reference electrode before the fluid sample makes contact with any part of the counter electrode; and
    (ii) a test meter for receiving said biosensor, said test meter including:

circuitry for producing a first signal when an electrical circuit is detected between the reference electrode and the working electrode;

circuitry for producing a second signal when an electrical circuit is detected between the counter electrode and at least one of the reference electrode and the working electrode;

a timer for determining the time interval between production of said first signal and said second signal; and a processor for triggering an error condition if said time interval exceeds a preset value or if said second signal is not produced within a preset time after said first signal is produced.

11. A test system comprising:

(i) a capillary-fill biosensor for indicating electrochemically the catalytic activity of an enzyme in the presence of a fluid sample containing an analyte acted upon by said enzyme;

the biosensor having a working electrode, a reference electrode and a counter electrode located within a capillary flow path between a fluid inlet and a fluid outlet;

the working electrode including a catalytically-active quantity of said enzyme;

wherein the reference electrode is separate from the counter electrode, and the reference and counter electrodes are arranged such that a fluid sample which flows evenly along the capillary flow path from said fluid inlet will substantially completely cover the reference electrode before the fluid sample makes contact with any part of the counter electrode; and (ii) a test meter for receiving said biosensor, the meter comprising:

means for making electrical contact with each electrode on said biosensor;

circuitry for performing an electrochemical measurement on said biosensor to produce a measured electrochemical value;

means for determining an analyte concentration value for a specified biological fluid from said measured electrochemical value; and means for indicating a determined analyte concentration value;

the meter further comprising:

first signal means for producing a first signal when an electrical circuit is detected between the reference electrode and the working electrode;

second signal means for producing a second signal when an electrical circuit is detected between the counter electrode and at least one of the reference electrode and the working electrode;

timing means for determining the time interval between production of said first signal and said second signal; and processing means for triggering an error condition if said time interval exceeds a preset value or if said second signal is not produced within a preset time after said first signal is produced.

12. A test meter for use with a biosensor, the meter comprising:

a first electrode contact for making an electrical connection with a working electrode on the biosensor;

a second electrode contact for making electrical contact with a reference electrode on the biosensor;

a third electrode contact for making an electrical connection with a counter electrode on the biosensor;

a processor for receiving an input signal from said electrode contacts;

a data store containing data relating to a specified biological fluid and accessible by said processor;

circuitry for measuring an electrical property of a fluid sample applied to a biosensor when the biosensor is inserted in the meter;

wherein the processor is arranged in operation to access the data store and to output an output signal representative of analyte concentration derived from the input signal and data contained in the accessed data store;

an output device for visually or audibly outputting information dependent on said output signal;

first signal circuitry for producing a first signal when an electrical circuit is detected between said first electrode contact and said second electrode contact;

second signal circuitry for producing a second signal when an electrical circuit is detected between said third electrode contact and at least one of said first electrode contact and said second electrode contact;

a timer for determining the time interval between production of said first signal and said second signal; and circuitry for triggering an error condition if said time interval exceeds a preset value or if said second signal is not produced within a preset time after said first signal is produced.

13. A test meter according to claim 12, further comprising:

a switch for releasably connecting the second electrode contact and the third electrode contact, the switch being closed before an electrical circuit has been detected; and switch-opening circuitry for opening the switch when an electrical circuit has been detected.

14. A test meter according to claim 13, wherein said switch-opening circuitry is a potentiostat circuit which makes a feedback loop when an electrical circuit has been made between the first electrode contact and the third electrode contact.

15. A test meter according to claim 13, wherein the second electrode contact will go open circuit when the switch is opened.

16. A test meter for use with a biosensor, the meter comprising:

a first electrode contact for making an electrical connection with a working electrode on the biosensor;

a second electrode contact for making electrical contact with a reference electrode on the biosensor;

a third electrode contact for making an electrical connection with a counter electrode on the biosensor;

a processor for receiving an input signal from said electrode contacts;

storage means containing data relating to a specified biological fluid and accessible by said processor;

means for measuring an electrical property of a fluid sample applied to a biosensor when the biosensor is inserted in the meter;

wherein the processor is arranged in operation to access the storage means and to output an output signal representative of analyte concentration derived from the input signal and data contained in the accessed storage means;

means for visually or audibly outputting information dependent on said output signal;

a switch for releasably connecting the second electrode contact and the third electrode contact, the switch being closed before a first electrical circuit has been detected;

potentiostat circuitry for opening the switch when said first electrical circuit has been detected, which will cause the second electrode contact to go open circuit;

said circuitry being adapted to make a feedback loop when a second electrical circuit has been made between the first electrode contact and the third electrode contact;

timing means for determining the time interval between detection of said first electrical circuit and detection of said second electrical circuit; and means for triggering an error condition if said time interval exceeds a preset value or if said second electrical circuit is not detected within a preset time after said first electrical circuit.

* * * * *